United States Patent
Bittmann et al.

Patent Number: 5,385,229
Date of Patent: Jan. 31, 1995

[54] CONTAINER FOR THE PACKAGING OF A HOLLOW ENDOPROSTHESIS

[75] Inventors: Peter Bittmann, Zürich; Fredy Tanner, Wil; Müller-Glauser, Wiesendangen, all of Switzerland

[73] Assignee: Sulzer Medizinaltechnik AG, Winterthur, Switzerland

[21] Appl. No.: 147,760

[22] Filed: Nov. 5, 1993

[30] Foreign Application Priority Data

Dec. 4, 1992 [EP] European Pat. Off. ........... 92810959

[51] Int. Cl.⁶ ............................................. A61F 2/00
[52] U.S. Cl. ...................................... 206/210; 206/439
[58] Field of Search ................ 206/210, 438, 439, 363, 206/828, 370

[56] References Cited

U.S. PATENT DOCUMENTS

| | | |
|---|---|---|
| 4,065,816 | 1/1978 | Sawyer . |
| 4,545,783 | 10/1985 | Vaughan ............... 206/438 X |
| 4,697,703 | 10/1987 | Will . |
| 4,750,619 | 6/1988 | Cohen et al. ........... 206/363 X |
| 4,838,288 | 6/1989 | Wright . |
| 4,863,016 | 9/1989 | Fong et al. ............. 206/439 X |
| 5,037,436 | 8/1991 | Heaston ................. 206/438 X |

FOREIGN PATENT DOCUMENTS

| | | |
|---|---|---|
| 0250904 | 1/1988 | European Pat. Off. . |
| 0281736 | 9/1988 | European Pat. Off. . |
| 0320441 | 6/1989 | European Pat. Off. . |
| 2587218 | 3/1987 | France . |
| 2132587 | 7/1984 | United Kingdom . |

*Primary Examiner*—Jacob K. Ackun, Jr.
*Attorney, Agent, or Firm*—Townsend and Townsend Khourie and Crew

[57] ABSTRACT

The container for packing hollow endoprostheses (8) comprises two germ-proof wrappings (1, 2). In accordance with the invention the inner wrapping (1) consists of a water-tight wall (10, 11) and various connection points (40, 50, 60). At least two of the connection points (40) are provided as access into the cavity of the prosthesis (8) and one is provided as an outlet (50) for liquids for treating the prosthesis. The outer wrapping (2) comprises through-pieces (42, 52, 62), which are associated with the connection points of the inner wrapping. The two wrappings are permeable to gas at least some regions. In accordance with the invention the container has a second application apart from its protective function: for example, in the case of a hybrid prosthesis for vascular replacement, to perform the charging of the prosthesis with the patient's own endothelial cells in the container.

14 Claims, 2 Drawing Sheets

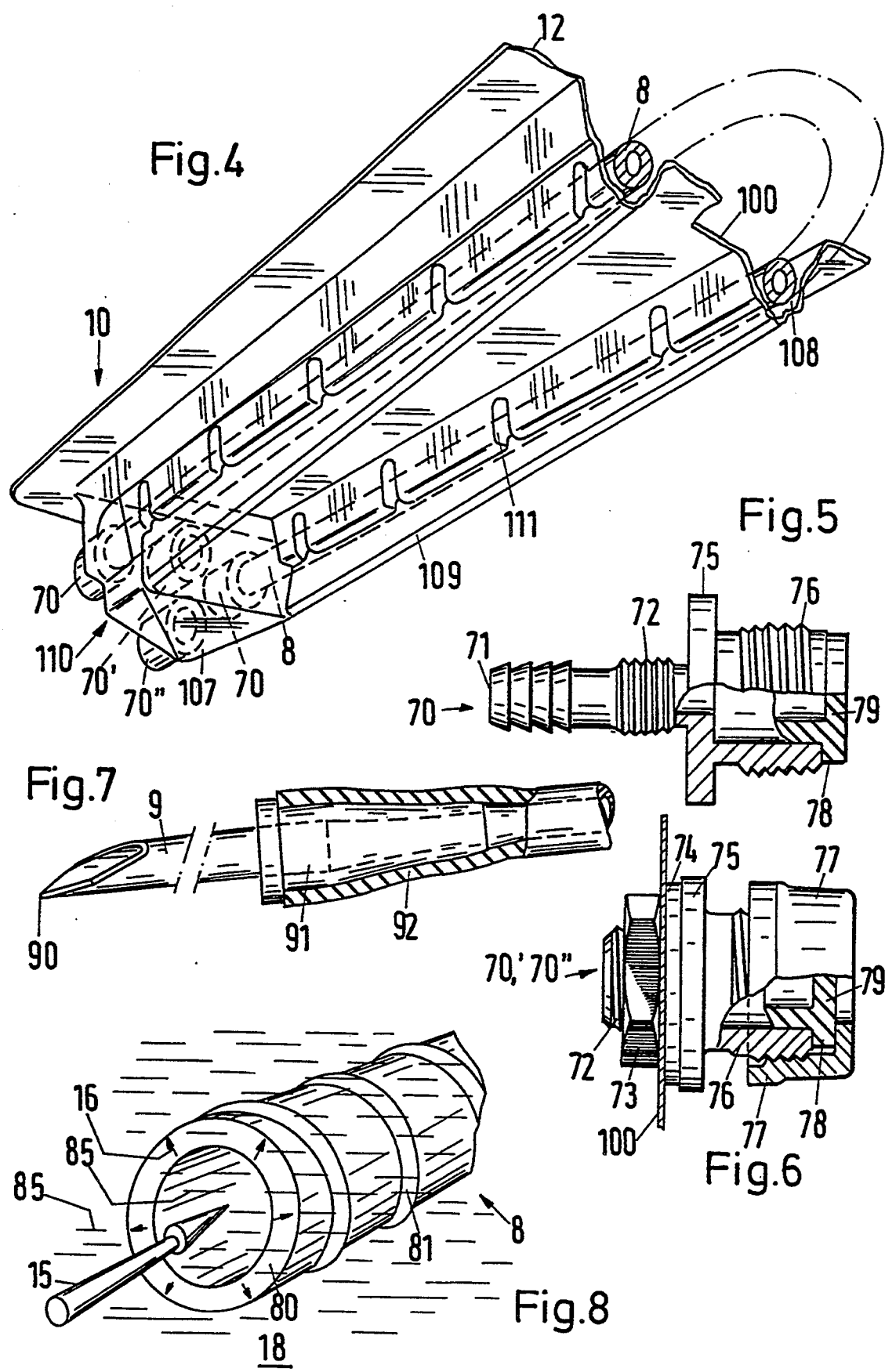

CONTAINER FOR THE PACKAGING OF A HOLLOW ENDOPROSTHESIS

BACKGROUND OF THE INVENTION

The invention relates to a container having two germproof wrappings for packaging a hollow endoprosthesis, in particular a hybrid prosthesis, which consists of an artificial, alloplastic component and from living endogenous cells, cell structures or tissue parts from the patient. Such prostheses are, for example, tubular support structures made from plastic, which are charged with the patient's own endothelial cells and are used as vascular replacements (see, for example, EP Patent Specification 0 320 441 = P.6146). Another example are endoprostheses, which are provided as organ replacements and which form support structures for living cells and/or other body parts, these prostheses being hollow but not necessarily tubular and comprising in addition a spongiform or reticular support structure in its cavity, for example, (see U.S. Pat. No. 4,963,489 (Naughton et al.) or German Offenlegungsschrift 39 36 568 (Schmidt).

When implants are inserted into human or animal bodies, sterility has to be guaranteed at all times. Germs which contaminate the implant can only be reached by the body's own defense system with difficulty or not at all and therefore can not be controlled either. Any site of infection which develops would unavoidably result in a repeat operation.

The requirements for the packaging protecting the implant vary depending on the retention site and the retention time. Temporary implants, which are used in the body's natural cavities or ducts, are mainly protected by just a single germproof wrapping. Implants which internally come into contact with human tissue, for example prostheses for tissue replacement, are normally protected from contamination by two germ barriers: by a primary packaging or product packaging and by a secondary packaging or protective packaging. Thanks to this double protection after the removal of the outer wrapping (protective packaging) the inner wrapping (product packaging), which is sterile on all sides, can be used without reservation in the sterile operating area.

SUMMARY OF THE INVENTION

The object of the invention is to create a container for a hollow endoprosthesis, in particular a hybrid prosthesis, which container is firstly used as packaging for which the sterility of the implant is guaranteed at all times and which secondly also permits the charging of the supporting structure, i.e. the alloplastic components, with living cells, cell structures or tissue parts from the patient.

With respect to the treatment of the prosthesis described below, it is pointed out that the prosthesis wall is porous and therefore is permeable to gas and water.

The production of the prosthesis and also the production of the container specified by the invention does not need to be carried out under sterile conditions. This is because sterilisation can be performed after the prosthesis has been packed into the double wrapping of the container (this packaging process naturally also includes the attachment of the prosthesis to the connection points of the inner wrapping). The choice of sterilization depends on the nature and the materials of the supporting structure. Steam sterilization or sterilization by means of gamma rays is advantageously chosen if the prosthesis and the materials used for the packaging can withstand such a treatment. Otherwise sterilization is carried out by means of ethylene oxide i.e. gas sterilization).

In the case of gas sterilization the ethylene oxide allowed to flow into the cavity of the prosthesis via at least one of the prosthesis connection points—and through the corresponding through-piece in the outer wrapping. Thanks to the gas permeability of the two wrappings and of the prosthesis wall the gas can spread out inside the container and the sterilizing action can begin.

Because the prosthesis is to be charged with living tissue, after gas sterilization it is indispensable that before charging the ethylene oxide is removed from the implant without any residue. This occurs—also thanks to the gas permeability of the two wrappings and the prosthesis wall—by repeated ventilation with sterile air (ventilation cycles).

After sterilization the prosthesis is ready for further preparatory steps, in which the prosthesis is treated by means of fluids. These procedural steps are described using the example of a tissue prosthesis; a corresponding process can also be used for the treatment of hollow organ prostheses. The example relates to a hybrid prosthesis, which is produced by charging a tubular, porous plastic wall with the patient's own endothelial cells and which comprises a partial seal of the wall by gelatine. (The term "prosthesis" relates to the synthetic wall, i.e. to the supporting structure, which can be charged with cells; "hybrid prosthesis" refers to the charged prosthesis.) The prosthesis in the example is sealed and sterilized in the container specified by the invention in the dry condition. The prosthesis can be stored packed in this way until its use.

The charging of the hybrid prosthesis, i.e. the extraction of patient's cells and also the coating of the plastic hose with these cells, has to be performed during the operation, in which vascular replacement occurs. A maximum time of one hour is available for the preparation of the hybrid prosthesis. The different steps required for this, e.g. the mechanical cutting of the patient's own starting tissue and also the subsequent enzymatic digestion, are performed in the form of a closed process in a machine, which is not described here. The container specified by the invention not only provides packaging and protection for the prosthesis, but at the same time is an integral component of this machine.

The following operational steps are to be performed during the preparation of the hybrid prosthesis for the operation:

1. The two connection points of the prosthesis, an overflow (if provided) and the outlet are connected to said machine by means of tubes.
2. The air is displaced from the cavity of the prosthesis by means of water.
3. A connection point of the prosthesis is sealed; water is supplied under pressure through the other connection point. In so doing water is forced through the prosthesis wall. When the outlet is closed the inner wrapping fills with water. The displaced air escapes through the air-permeable regions of the wrapping walls and if necessary through the overflow. Finally the prosthesis is completely under water; a holding-down device prevents the prosthesis from coming to the surface.

4. During a waiting period of five to ten minutes the gelatine wells into the prosthesis wall. (i.e. "equilibrium" of the prosthesis. If a prosthesis is charged without a gelatine seal this step is omitted.)
5. A suspension of the endothelial cells is pumped into the cavity of the prosthesis and forced through the prosthesis wall. During this the cells become deposited on and in the wall, i.e. on the supporting structure. So that the charging operation occurs evenly, the prosthesis has to be disposed horizontally as far as possible.
6. The overflow is opened so that the inner wrapping is emptied.
7. After the removal of the inner wrapping the prosthesis is "radially" rinsed, i.e. during a flow through the prosthesis wall. The outlet is again closed, so that the inner wrapping is filled with the rinsing fluid.
8. After repeated emptying of the inner wrapping, radial rinsing is repeated. The purpose of the rinsing is to remove as completely as possible substances which are dissolved in the cell suspension (in particular the enzyme used to digest the tissue).
9. Finally the prosthesis is "axially" rinsed by the rinsing fluid being permitted to leave via the second connection point.

After this preparation of the prosthesis the outer wrapping (protective wrapping) is opened. The charged prosthesis, which is encased in the product packaging, which is germ-free on all sides, can now be taken out of the opened wrapping and be brought into the sterile operation area. The invention is explained in more detail below by drawings.

BRIEF DESCRIPTION OF THE FIGURES

FIG. 4 shows a lower view of a tray, which forms the inner wrapping for a second embodiment, FIG. 5 shows a component of a connection point for the prosthesis sealed with a membrane, FIG. 6 shows a through-piece with membrane seal, FIG. 7 shows a hollow needle with tube and FIG. 8 shows a short piece of a vascular prosthesis.

DESCRIPTION OF THE PREFERRED EMBODIMENTS

Figure 1:
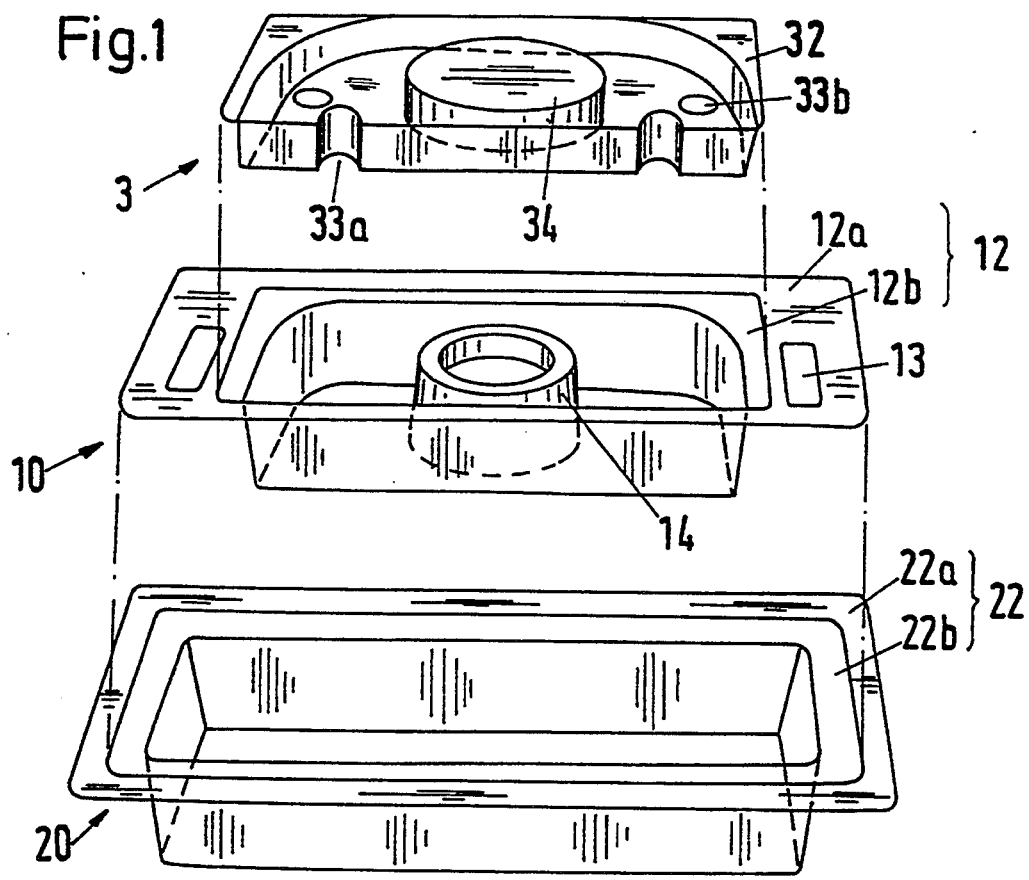
FIG. 1 shows an exploded view with three parts of a first embodiment of the container according to the invention.
Figure 2:
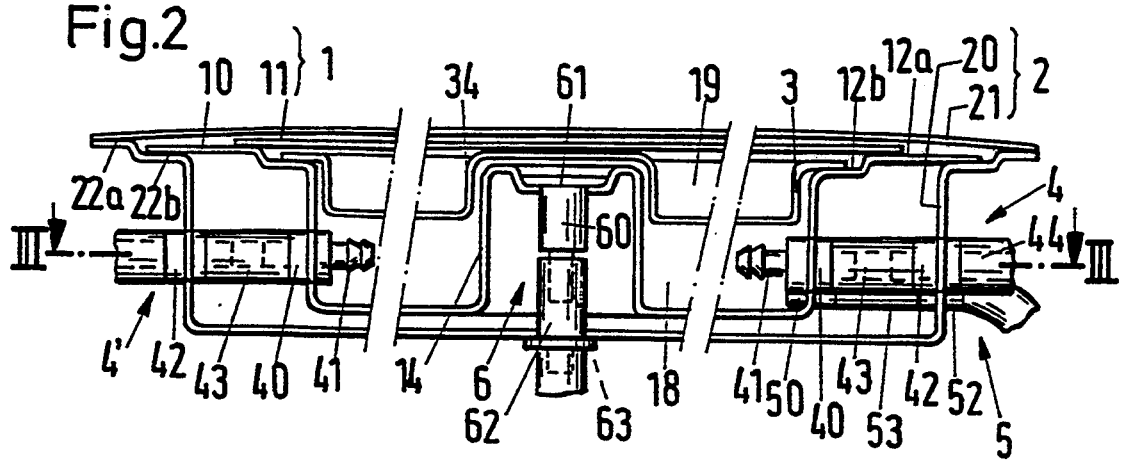
FIG. 2 shows a vertical cross section through the container of FIG. 1 (without prosthesis), along line (II—II in FIG. 3

The inner wrapping 1 (product packaging) shown in FIGS. 1 and 2 consists of a tray 10 and a lidding foil 11 and the outer wrapping 2 (protective packaging) consists of a tray and a lidding foil 21. The lidding foils 11 and 21 are connected to the edges 12 and 22 respectively of the corresponding trays 10 and respectively 20, and in fact with the edge zones 12a and 22a respectively and can be peeled off. The edge 22 of the outer tray 20 comprises a cavity 22b, into which the edge 12 of the inner tray 21 inserted. The inner tray 21 comprises a corresponding cavity for a holding-down device 3.

Figure 3:
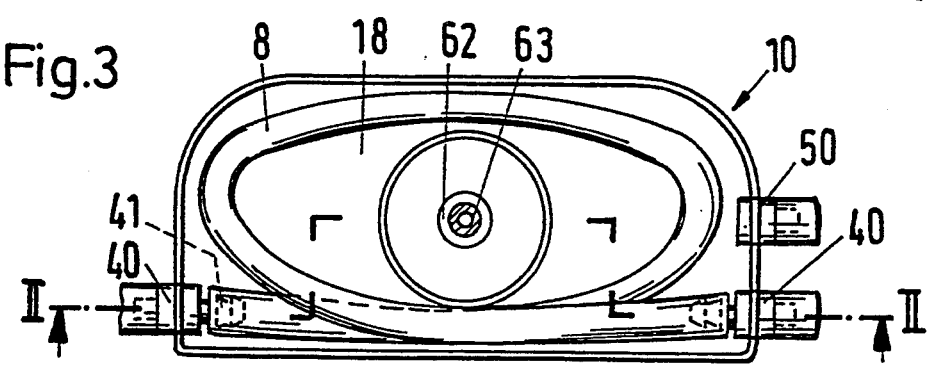
FIG. 3 shows a horizontal cross section through the inner wrapping of the same container (with prosthesis), along line III—III in FIG. 2.

From the inner wrapping 1 extend multi-part connection pieces 4, 4', 5 and 6 to the outside of the outer wrapping 2. (In FIG. 1 for the sake of simplicity neither these connection pieces nor openings which are provided for them are shown.) Connection piece 4 consists of a connection point 40 having a fitting 41 for the prosthesis 8 (FIG. 3), a through-piece 42 in the outer wrapping 2 and a connecting tube piece 43. A tube 44 is connected to the through-piece 42. (For the storage of the packaged prosthesis instead of the hose 44 there is provided a sealing cap, which prevents the contamination of the interior of the container.) The other end of the prosthesis 8 is connected to a second connection piece 4', which has the same construction as connection piece 4. A similar connection piece 5 is provided for an outlet 50. In the middle of the inner tray 10 a cylindrical wall piece 14 together with a connection piece 6 forms an overflow, which is constructed from a connection point 60 with an overflow outlet 61, a through-piece 62 in the outer wrapping 2 and a plug-in connection 63.

The purpose of the holding-down device 3 is to prevent the prosthesis rising to the surface in the preparatory steps described above. Lateral ducts 33a and openings 33b ensure good permeability for gas and fluid between the prosthesis chamber 18 (FIG. 2) and the space 19 between the holding-down device 3 and the lidding foil 11.

The lower parts of the two wrappings 1 and 2 are moulded trays 10 and 20 respectively, which are advantageously produced by hot forming from thermoplastic sheeting. The lidding foils 11 and 21 are gas-permeable and are advantageously made from a tear-resistant paper-like material, for example "Tyvek" (trade name). The lidding foils may be connected to the trays by welding, whereby an easily separable connection is provided, which enables the lidding foils to be peeled off.

So that the inner wrapping 1 can be removed after the outer wrapping 1 has been opened, the connections between the connection points 40, 50 of the wrapping 1 and the through-pieces 42, 52 (FIG. 2) of the wrapping 2 have to be broken. For this purpose apertures 13 are provided in the edge 12 of the tray 10, so that the tubular pieces 43, 53 can be cut by means of scissors through these apertures 13. The connection of the overflow 6 is broken by withdrawing the plug-in connection 63.

In the embodiment shown in FIG. 4, the connection points 70 (prosthesis connections), 70' (overflow) and 70'' (outlet) are disposed on one side 110 of the tray 10. With respect to the mentioned machine, with which the charging of the prosthesis is performed, this arrangement is more expedient than that of the first embodiment, as the connection to the machine can be produced with a type of plug—similar to an electric plug. The prosthesis 8 lies in a U-shaped horizontal conduit 108, which is covered by a holding-down device (not shown). Beneath the conduit 108 are provided two outlet channels 109, which lead into a sump 107 at outlet 70''. Ribs 111 in the conduit 108 ensure that the prostheses 8 only comes into contact with the wall 100 at these ribs 111.

As in the first exemplified embodiment, the connection points 70, 70' and 70'' may be connected to through-pieces in the outer wrapping (not shown) via tubular parts. However it is possible for these connection points and through-pieces respectively to use the components shown in FIGS. 5 and 6, in which the connection is produced by means of a hollow needle 9 (FIG. 7):

The connection point 70 for the prosthesis consists of the following parts (see FIG. 5 and FIG. 6): fitting 71 for the prosthesis; thread 72 for a nut 73 (for the attachment of the tray 10 to the wall 100); sealing ring 74; flange 75; membrane support 76 with union nut 77 and membrane stopper 78; membrane 79 (made from an elastomer material). The connection points 70' and 70" for the overflow and outlet respectively (FIG. 6) differ from the prosthesis connection points 70 essentially only by the missing fitting 71. The component in FIG. 6 is also suitable as a through-piece in the outer wrapping. The through-piece and the associated connection point of the inner wrapping 10 are aligned, so that the connection can be produced with a hollow needle 9 (FIG. 7). The hollow needle 9 has a sharp point 90 for piercing the two membranes 79; and it is connected to a tube 92 via a reducing fitting 91. The connections of the prosthesis naturally have to be manufactured from materials compatible with cells.

The second embodiment of the container according to the invention has two important advantages when compared with the first embodiment, which relate to preparatory steps 3 (flooding the inner wrapping) and 7 and 8 (rinsing):

1. the conduit 108 has a significantly smaller volume than the prosthesis chamber 18.
2. the channels 109 and the sump 107 permit better emptying. Thanks to these advantages less liquid is required for treating the prosthesis. Preparatory step 3 lasts a shorter time and steps 7 and 8 are more thorough.

FIG. 8 is a supplementary illustration of the preparatory steps 3, 5, 7 and 8. A liquid 85 is axially supplied (arrow 15) to the prosthesis 8 lying horizontally in chamber 18, with the porous wall and a helical inner wall 81. The liquid 8 flows radially from the cavity 82 of the prosthesis 8 into the environment (arrows 16). As the prosthesis 8 is completely surrounded by the liquid 85, a largely constant radial flow is produced over the periphery. Therefore in the event of the liquid 85 being the cell suspension, there is uniform cell charging of the prosthesis wall 80, both in the circumferential direction and also in the longitudinal direction.

We claim:

1. A container for packing a prosthesis comprising:
a sterile inner wrapping surrounding a chamber shaped for receiving the prosthesis, the inner wrapping having a fluid-tight wall with at least one gas-permeable region;
a sterile outer wrapping substantially enclosing the inner wrapping and having at least one gas-permeable region; and
first and second inner ports in the inner wrapping fluidly coupled to first and second outer ports, respectively, in the outer wrapping for providing fluid access to the chamber.

2. The container of claim 1 wherein the wrappings each comprise a molded tray and a gas-permeable lid, the inner and outer ports extending through the trays.

3. The container of claim 2 wherein the lids are removably attached to the trays.

4. The container of claim 2 wherein the trays each comprise a hot formed sheet of thermoplastic material.

5. The container of claim 1 further comprising an overflow port in the inner wrapping, a third outer port in the outer wrapping, and a connection plug fluidly coupling the overflow port to third outer port and tubes fluidly coupling the first and second inner ports to the first and second outer ports.

6. The container of claim 5 wherein the inner and outer ports comprise an elastomeric seal and a hollow tube extending through the seal.

7. The container of claim 1 further comprising holding means, positionally fixed within the inner wrapping, for securing the prosthesis within a fixed area in the inner wrapping.

8. The container of claim 1 wherein the inner and outer wrappings have a generally rectangular shape with first and second ends, the inner and outer ports being disposed on one of the first and second ends.

9. The container of claim 1 wherein the inner wrapping further comprises a sump fluidly coupled to the third inner port for collecting overflow fluid exiting the third inner port.

10. The container of claim 9 wherein the inner wrapping further comprises channels fluidly coupling the sump to the third inner port.

11. A storage system comprising:
a vascular prosthesis charged with a patient's endothelial cells; and
a container for housing the prosthesis comprising:
a sterile inner wrapping enclosing the prosthesis and having a fluid-tight wall with portions that are gas-permeable and at least one inner opening providing fluid access to the prosthesis; and
a sterile outer wrapping enclosing the inner wrapping and having at least one outer opening coupled to the inner opening, the outer wrapping having portions that are gas-permeable.

12. A method for preparing a hybrid prosthesis for implantation into a patient's body comprising the steps of:
(a) housing the prosthesis in a chamber enclosed by an inner wrapping having a fluid-tight wall with at least one gas-permeable region and having first and second inner ports, the inner wrapping being enclosed by an outer wrapping having at least one gas-permeable region and first and second outer ports fluidly coupled to the inner ports;
(b) connecting at least the first outer port to a fluid delivery source;
(c) sealing the second inner port;
(d) pumping water through the first inner and outer ports to force the water through an outer wall of the prosthesis into a hollow bore within the prosthesis, the water displacing air from the chamber through the gas-permeable regions of the inner and outer wrappings;
(e) securing the prosthesis to a fixed position within the inner wrapping so that the prosthesis is enveloped by the water;
(f) pumping a suspension of endothelial cells from the patient through the first inner and outer ports to force the endothelial cells into the outer wall of the prosthesis; and
(g) opening an overflow port to allow the water to exit the chamber.

13. The method of claim 12 further comprising the steps of:
(h) closing the overflow port;
(i) pumping water through the first inner and outer ports to direct water in a radial direction through the outer wall of the prosthesis, the water removing substances dissolved in the endothelial cell suspension from the outer wall of the prosthesis;
(j) opening the overflow port to allow the water to exit the chamber;

(k) repeating steps (h), (i) and (j) until the substances are substantially removed from the prosthesis;

(l) opening the second inner port; and (m) pumping water through the second inner and outer ports into the chamber, the water flowing past the prosthesis in an axial direction and exiting through the first inner and outer ports to further remove the substances from the prosthesis.

14. A container for packing a prosthesis comprising:

a sterile inner wrapping surrounding a chamber that is adapted for the prosthesis, the inner wrapping having a water-tight wall with inner and outer surfaces and at least one gas-permeable region;

a sterile outer wrapping completely enclosing the inner wrapping so that the outer surface of the inner wrapping remains sterile, the outer wrapping being removable from the inner wrapping and having at least one gas-permeable region; and at least one opening in the inner wrapping fluidly coupled to at least one opening in the outer wrapping for providing fluid access to the chamber.

* * * * *